United States Patent
Gershlick

(10) Patent No.: US 8,876,887 B2
(45) Date of Patent: Nov. 4, 2014

(54) COLLAPSIBLE STENT

(75) Inventor: Anthony Harvey Gershlick, Barkby (GB)

(73) Assignee: University Hospitals of Leicester NHS Trust, Leicester (GB)

( * ) Notice: Subject to any disclaimer, the term of this patent is extended or adjusted under 35 U.S.C. 154(b) by 128 days.

(21) Appl. No.: 12/602,859

(22) PCT Filed: Jun. 5, 2008

(86) PCT No.: PCT/GB2008/001922
§ 371 (c)(1),
(2), (4) Date: Apr. 12, 2010

(87) PCT Pub. No.: WO2008/149094
PCT Pub. Date: Dec. 11, 2008

(65) Prior Publication Data
US 2010/0211163 A1    Aug. 19, 2010

(30) Foreign Application Priority Data

Jun. 8, 2007  (GB) .................................. 0711122.2

(51) Int. Cl.
*A61F 2/86* (2013.01)
*A61F 2/88* (2006.01)
*A61F 2/82* (2013.01)
*A61F 2/91* (2013.01)

(52) U.S. Cl.
CPC ... *A61F 2/86* (2013.01); *A61F 2/88* (2013.01); *A61F 2002/821* (2013.01); *A61F 2250/0018* (2013.01); *A61F 2/91* (2013.01); *A61F 2250/0029* (2013.01)
USPC ........................................ 623/1.15; 623/1.22

(58) Field of Classification Search
CPC ............. A61F 2/86; A61F 2/88; A61F 2/915; A61F 2002/821; A61F 2250/0018; A61F 2250/0029
USPC ......... 606/108, 191, 194, 200; 623/1.11–1.54
See application file for complete search history.

(56) References Cited

U.S. PATENT DOCUMENTS

| | | | | |
|---|---|---|---|---|
| 5,496,365 A | * | 3/1996 | Sgro | 623/1.2 |
| 5,554,181 A | * | 9/1996 | Das | 623/1.12 |
| 5,591,197 A | * | 1/1997 | Orth et al. | 623/1.16 |
| 5,607,444 A | | 3/1997 | Lam | |
| 6,017,365 A | * | 1/2000 | Von Oepen | 623/1.15 |
| 6,270,524 B1 | * | 8/2001 | Kim | 623/1.15 |

(Continued)

FOREIGN PATENT DOCUMENTS

| | | |
|---|---|---|
| AR | 047110 | 10/2004 |
| EP | 0812580 | 12/1997 |

(Continued)

OTHER PUBLICATIONS

"Bifurcated Stents: Giving to Caesar What is Caesar's," Alexandre Abizaid et al., EuroInterv. 2007; 2:518-525.

*Primary Examiner* — Kathleen Holwerda
(74) *Attorney, Agent, or Firm* — Price Heneveld LLP

(57) ABSTRACT

A stent suitable for the repair of lesions in bifurcated blood vessels is provided, having a deformable end portion such that a free end of the end portion can be aligned with the surface of an abutting stent or angioplasty balloon in a main branch of the bifurcated vessel. A method of blood vessel repair using this stent is also provided.

20 Claims, 5 Drawing Sheets

(56) References Cited

U.S. PATENT DOCUMENTS

| | | | |
|---|---|---|---|
| 6,461,320 B1 * | 10/2002 | Yencho et al. | 604/8 |
| 6,485,510 B1 * | 11/2002 | Camrud et al. | 623/1.16 |
| 6,488,703 B1 * | 12/2002 | Kveen et al. | 623/1.15 |
| 6,673,107 B1 | 1/2004 | Brandt et al. | |
| 6,945,992 B2 * | 9/2005 | Goodson et al. | 623/1.13 |
| 2002/0173840 A1 | 11/2002 | Brucker et al. | |
| 2004/0172126 A1 | 9/2004 | Hojeibane | |
| 2004/0225345 A1 | 11/2004 | Fischell et al. | |
| 2005/0028877 A1 | 2/2005 | Zanolin et al. | |
| 2005/0222672 A1 | 10/2005 | Shmulewitz | |
| 2006/0079956 A1 * | 4/2006 | Eigler et al. | 623/1.35 |
| 2007/0061003 A1 | 3/2007 | Shmulewitz et al. | |

FOREIGN PATENT DOCUMENTS

| | | |
|---|---|---|
| EP | 1173109 | 9/2006 |
| EP | 1723932 | 11/2006 |
| EP | 1847236 | 10/2007 |
| FR | 2678508 | 1/1993 |
| JP | 4336049 | 9/2009 |
| WO | 0051523 | 9/2000 |
| WO | 2005034809 | 4/2005 |
| WO | 2005096996 | 10/2005 |
| WO | 2007070140 | 6/2007 |

* cited by examiner

US 8,876,887 B2

COLLAPSIBLE STENT

FIELD OF THE INVENTION

The present invention relates to a stent for use at bifurcations, and particularly but not exclusively for repairing bifurcated blood vessels that are diseased.

BACKGROUND OF THE INVENTION

Conventional stents for blood vessel repair are generally hollow and cylindrical in shape and have terminal ends that are perpendicular to the longitudinal axis. In use, such a stent is positioned at the diseased area of the vessel and, after placement, the stent provides an unobstructed pathway for blood flow. Placement of the stent may generally be achieved by using an elastic material for the stent with the stent retained in a curled up configuration inside a sheath such that the stent expands when the sheath is removed. Alternatively, a memory material such as NiTi which expands to a previously defined position on a change in ambient temperature can be used. Probably most common, the stent may be made of a malleable material and in a configuration such that it can be expanded by an angioplasty balloon catheter inside it.

When attempting to repair a lesion at a bifurcation of a blood vessel, the following problem arises. Because the terminal ends of conventional stents are perpendicular to the longitudinal axis, it is only possible to repair a lesion at the bifurcation completely without obstructing the blood flow downstream from the bifurcation if the side branch vessel extends from the main vessel at an angle of 90 degrees. This is unlikely to be the case in anatomical conditions.

In any anatomical bifurcation at which the side branch extends at an angle different from 90 degrees from the main branch, the repair will either be incomplete if one edge of the terminal end of the conventional stent is placed at the ostium in the main vessel or the main vessel obstructed by one edge of the terminal end if the conventional stent is to fully cover the side branch.

Various systems and methods have been proposed in order to overcome the problem outlined above. In a first approach, a conventional stent is advanced through the side branch and placed such that it fully covers the side branch vessel wall and ostium, meaning that a substantial portion of it will protrude into the lumen of the main vessel. In a second step, a balloon is advanced down the main vessel and expanded to crush the protruding stent material against the vessel wall of the main branch adjacent to the ostium. In a third step, a second stent is advanced down the main branch and placed adjacent to the ostium using a balloon which is then backed up and, in a fourth step, is advanced into the side branch and expanded to open up an aperture in the stent corresponding to the ostium. This procedure relies on the main branch vessel wall to be sufficiently stable to allow the protruding end to be crushed against it, which clearly bears a risk of injuring the vessel. Moreover, there is a significant risk of dislodging the atheroma and other material forming the lesion to be repaired which bears a risk of causing a heart attack in the patient.

US2006/0079956 (Eigler et al) shows one example of this approach of crushing a protruding portion of a side branch stent against the main branch vessel wall. A proximal portion of the side branch stent is arranged to be more easily crushable for this purpose.

An alternative known approach relies on two stents with corresponding balloon catheters being advanced down the main branch, whereby the catheter of a trailing one of the stents is threaded through the leading stent. As the assembly approaches the side branch, the catheter of the leading stent is threaded into the side branch and the catheter of the trailing stent is advanced past the ostium remaining in the main branch. Following placement of the leading stent, such that it is partially inside the main branch and partially inside the side branch, the trailing stent is advanced through the leading stent guided by its catheter and is then placed partially inside the leading stent and partially inside the main branch beyond the ostium to, in essence, implement a T-shaped stent arrangement. This approach also has a significant drawback in that two stents need to be sequentially advanced through the main branch, which requires careful manipulation of the two catheters such that each one is placed in the correct branch and in that a double layer of stent material (two stents overlapping each other) remains in the main branch resulting in a greater risk of complications. An example of this two stent approach can be found in US2004/0172126 (Hojeibane).

An alternative stent for repairing a vessel at a bifurcation without obstructing blood flow through the bifurcation is disclosed in U.S. Pat. No. 5,607,444 (Lam). The stent includes a flaring portion intended to cap the ostium of the bifurcation. However, the flaring portion does not fully cover the vessel walls surrounding the ostium and the stent requires a specifically shaped balloon to be placed. Moreover, this may be less suitable for a lesion which extends substantially both within a side branch and a main branch of a bifurcated vessel.

A discussion of known side branch stents and methods can be found in "Bifurcated Stents: giving to Caesar what is Caesar's", Alexandre Abizaid et al, EuroInterv. 2007; 2:518-525.

SUMMARY OF THE INVENTION

In an aspect of the invention, there is provided a stent comprising a deformable end portion.

By being able to dispose the end plane of an end-portion of the stent in an angled relationship with the vessel-supporting wall of the stent (or more generally, allowing the vessel supporting wall to longitudinally collapse more on one side than on another), a more efficient and easier method of repairing lesions at bifurcated vessels can be enabled.

The end portion may, for example, be implemented with expandable rings secured to each other by collapsible webs such that the rings can expand and the web collapse in order to allow the end plane to be angled. Expansion of the rings may be enabled by providing the rings in a folded configuration within the vessel supporting wall and the collapsible webs may be jointed to enable them to fold onto themselves when collapsing. When collapsing, the webs may move inside the vessel-supporting wall or they may move such as to protrude, for example, to the outside of the vessel-supporting wall, providing further anchorage for the stent.

The stent may either comprise the same arrangement as the end portion throughout or it may comprise a main portion different from the end portion, for example, of a conventional stent arrangement. Both the main portion and end portion or only one of them may be manufactured from a tubular member of suitable material by machining away material, for example by laser cutting, to define the respective portions.

BRIEF DESCRIPTION OF THE DRAWINGS

Embodiments of the invention are now described by way of example only and with reference to the accompanying drawings in which.

DETAILED DESCRIPTION OF THE PREFERRED EMBODIMENT

Figure 1:
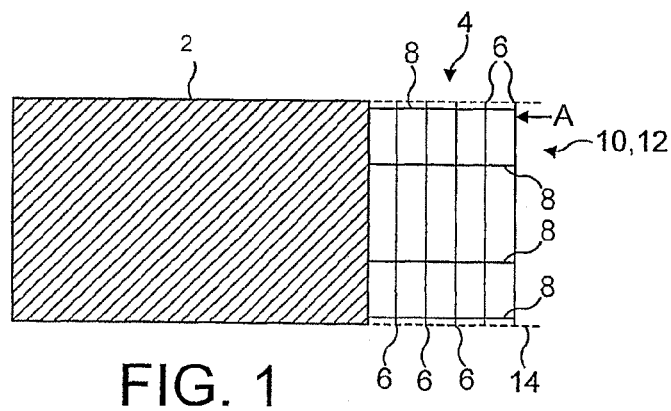
FIG. 1 is a schematic view of a side elevation of a stent having a deformable end portion.
Figure 2:
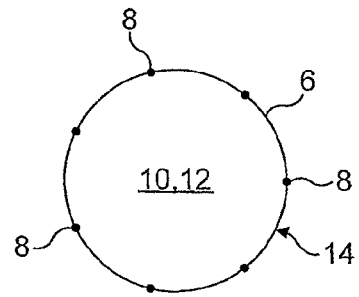
FIG. 2 is a schematic frontal view of the stent of FIG. 1 along an arrow A in FIG. 1.

With reference to FIG. 1, a vascular stent in accordance with an embodiment of the present invention (in its expanded state) comprises a main portion 2 and an end portion 4. The main portion may comprise any conventional stent design but in one specific embodiment comprises a stent portion designed to be placed by expansion using an angioplasty balloon. The end portion 4 comprises a plurality of rings 6 secured to each other and to the main portion 2 by webs 8. The end portion may be substantially shorter than the main portion 2. For example, it may be a third of the overall length of the stent. FIG. 2 depicts a frontal view along arrow A showing the foremost one of the rings 6 and the corresponding webs 8 schematically.

A free end 10 of the end portion 4 defines an end plane 12. For example, if the free end 10 is planar, it lies in an end plane 12. As described in more detail below, the webs 8 are arranged to be collapsible such that the end plane 12 can be tilted with respect to a notional vessel-supporting wall 14 (directed along a longitudinal axis) indicated in the drawings by dotted lines and defined by the circumference of the rings 6. The vessel-supporting wall 14 is oriented generally along the longitudinal axis defined by the main and end portions 2 and 4.

In response to an uneven pressure on the free end 10, the collapsible webs 8 allow the free end 10 to yield and responds to the uneven pressure such that it comes to rest in an angled relationship with respect to the vessel-supporting wall. Therefore, if the free end is pressed against a surface (or a surface is pressed onto the free end) such that the surface is angled or tilted with respect to the vessel-supporting wall 14, the free end will yield such that the end plane is aligned with the surface and hence tilted with respect to the vessel-supporting wall 14 and, by definition, the longitudinal axis of the main body of the stent. The term "angled" is used here in the sense of "tilted", that is an angle different from 0, 90, 180 or 270 degrees.

As the free end 10 tilts in response to an uneven pressure, the remaining rings 6 will also tilt at some point, at least if one side of the end portion is collapsed by more than the length of a single web 8. As the rings 6 progressively tilt with respect to the vessel-supporting wall 14, the end portion 4 can thus be seen as a concertina-like extension of the main portion 2 allowing the free end 10 to adapt to the attitude of an abutting surface.

As the free end 10 (or any other of the rings 6) tilts with respect to the vessel-supporting wall 14, there is a tendency for the cross section of the end portion to be reduced because the area of the diagonal section defined by the tilted end plane 12 is larger than the area of a cross section of the end portion.

In order to allow for maximum flow volume to remain available, the rings 6 are themselves deformable in one embodiment and can expand to accommodate the larger (ellipsoid) surface of the angled section.

Figure 4:
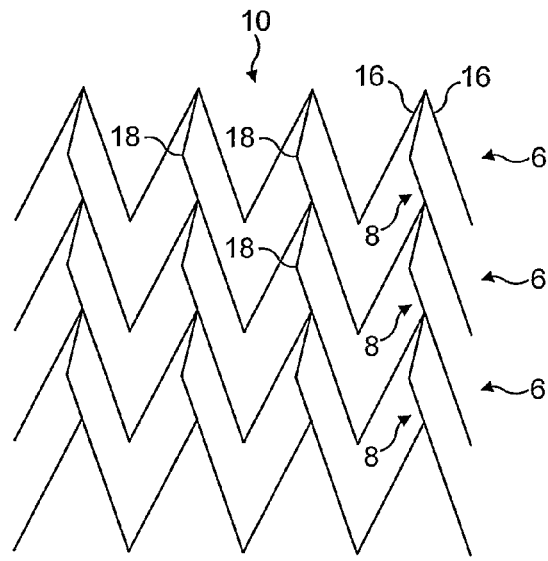
FIG. 4 schematically depicts an exemplary implementation of the end portion of the stent in an initial state.
Figure 5:
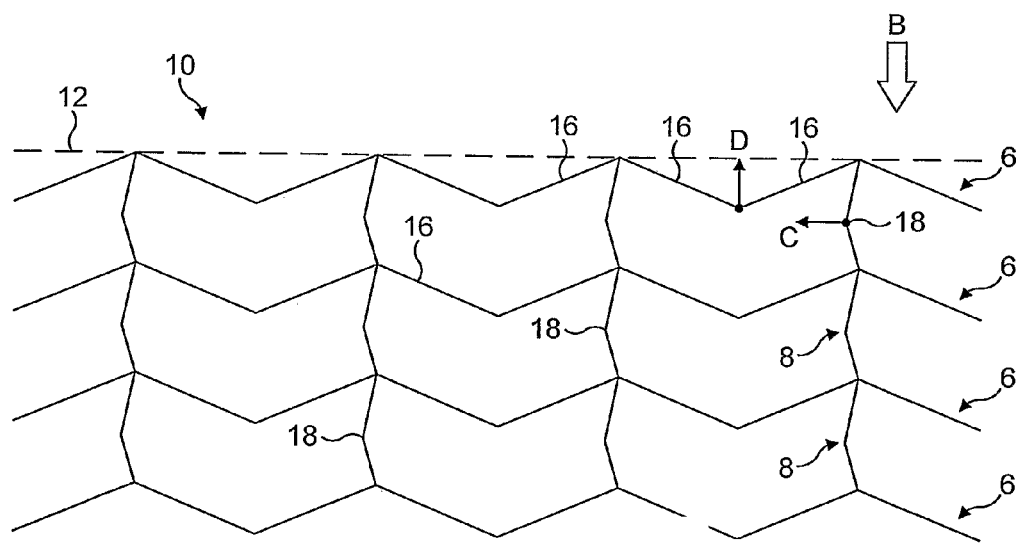
FIG. 5 depicts schematically the implementation of FIG. 4, when expanded.

With reference to FIGS. 4 and 5, a detailed, developed view of part of the end portion in FIG. 1 illustrates the arrangement of the rings 6 and webs 8 in one specific implementation. FIG. 4 shows a part of the end portion in its initial state and FIG. 5 shows the corresponding expanded state. It will be understood that FIGS. 4 and 5 are schematic representations and that the lines and angles depicted may, respectively, be curved (or differently shaped) and rounded.

The rings 6 include a series of folds 16 folded up onto each other within the vessel-supporting wall. It will be understood that, while FIGS. 4 and 5 show a developed view of only a few folds 16, the folds 16 extend circumferentially around the end portion 4 to form a closed loop defining the rings 6. The webs 8 extend between and link adjacent rings 6 and it should be noted that although this specific implementation is depicted with the webs 8 joining peaks of the folds 16, it is equally envisaged that the webs may join the rings 6 at any other location. The webs 8 are also folded onto each other to define a pre-defined kink 18 which allows the webs to collapse, as described above and fold onto themselves.

As mentioned above, FIG. 4 shows the initial state of the stent. Once the stent is located in position, it can be expanded, for example, by inflating an angioplasty balloon inside the stent to expand it to its expanded state depicted in FIG. 5. As the stent is expanded in a radial direction as the balloon is inflated, the rings 6 undergo an unfolding transformation to accommodate the increased circumference associated with the radial expansion. The radial expansion does not effect the longitudinal distances between the rings 6 such that the configuration of the webs is not changed substantially during expansion, although there will be a small longitudinal shrinkage of the end portion as the angles between folds 16 flatten.

The yielding action of the end portion 4 is now described with reference to the expanded state depicted schematically in FIG. 5. As uneven pressure indicated by arrow B is applied to a portion of the free end 10, the webs 8 to which most pressure is applied yield by folding onto themselves resulting in motion of the kinks 18 as indicated by arrow C. At the same time, the expanding circumference of the increasingly slanted section of the vessel-supporting wall 14 as the end plane 12 tilts is accommodated by expansion of the rings 6 by further unfolding of the folds 16 resulting in a motion as indicated by the arrow D.

It will be understood that the principle motion of the end portion 4 is the concertina-like adaptation of the end plane 12 to uneven pressure and/or a tilted contact surface and that exact adaptation of the circumference of rings 6 to the slanted sections due to the angle of the end plane 12 with the vessel-supporting wall 14 is not required. Similarly, the motion of kinks 18 indicated by arrow C may be tangentially with respect to the vessel-supporting wall 14 or may be arranged to be perpendicular to it. In the former case, the vessel-supporting wall remains relatively smooth. In the latter case, the kinks 18 may provide further anchorage for the end portion of the stent if they are arranged to protrude from the vessel-supporting wall 14 on folding.

More generally, the deformation of the free end 10 need not be limited to a tilting motion of an end plane. The end portion may be deformed more generally such that at certain points of the circumference of the free end (where more pressure is applied) the vessel wall collapses longitudinally by a larger amount than at other points (where less pressure is applied). For example, the end portion may collapse longitudinally only at specific points of the circumference, say only on one side, while not collapsing at other points (say on another side).

Figure 6:
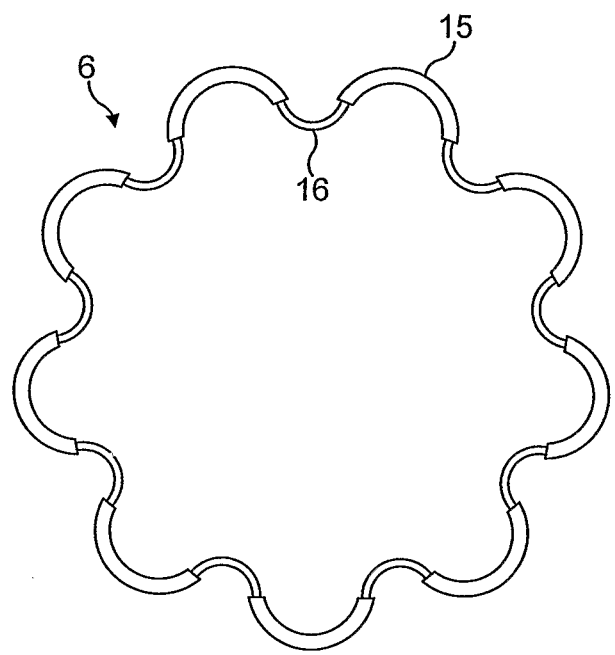
FIGS. 6 and 7 depict schematically an alternative implementation of the end portion.
Figure 7:
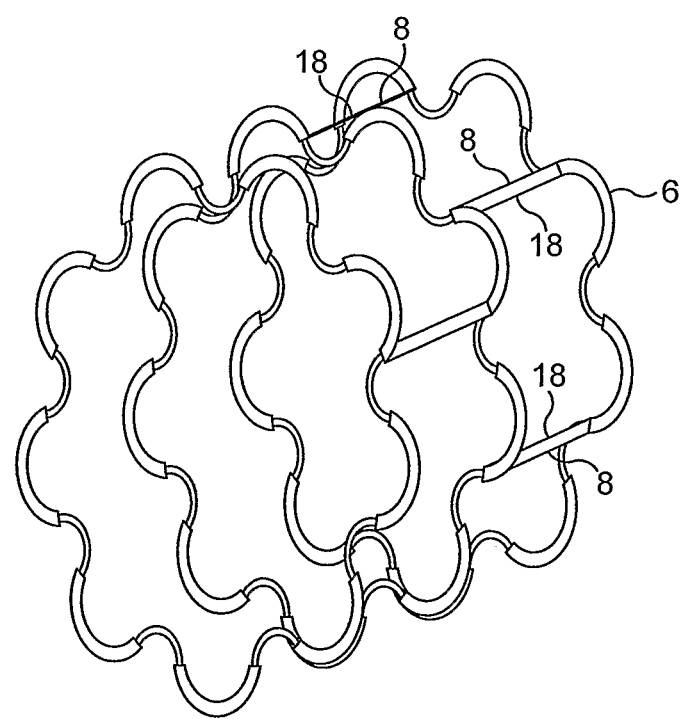

An alternative implementation of the end portion 4 is now described with reference to FIGS. 6 and 7. In this embodiment, the ring 6 includes major 15 and minor 16 arcuate members connected to each other such that their respective arcs point in opposite directions. The pairs of arcuate members allow an expanding action in the same way as folds 16. To form the end portions, the rings 6 are joined by webs 8 having a predetermined kink 18 to fold under pressure, as described above.

Figure 8A:
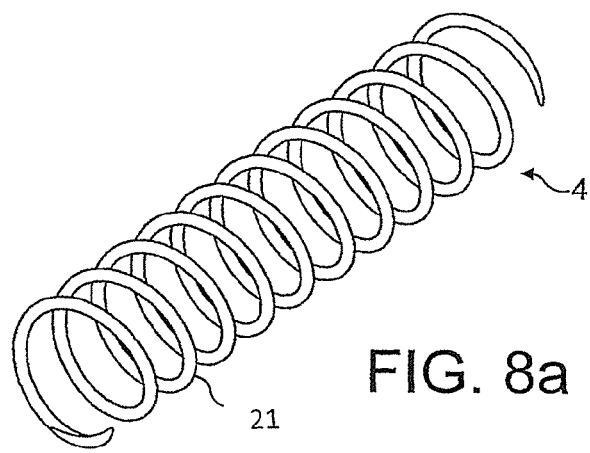
FIGS. 8a, 8b and 9 depict schematically a further alternative implementation of the end portion.

A further alternative implementation of the end portion 4 is now described with reference to FIGS. 8a and b and FIG. 9. In this alternative implementation, the end portion 4 defines a spiral 20 having a plurality of turns to enable the end portion to collapse longitudinally as described above due to its inherent elasticity and/or malleability. It will, of course, be understood that the spiral 21 does not require joining webs to define its structure, but for further structural stability the turns of the spiral may be linked by one or more webs 8 having a predetermined kink 18 to fold under pressure as described above. The spiral may be manufactured using known techniques such as laser cutting in its expanded state from a metal having a shape memory, for example an elastic or temperature activated shape memory. For example, the shape memory metal may be Nitinol.

Figure 9:
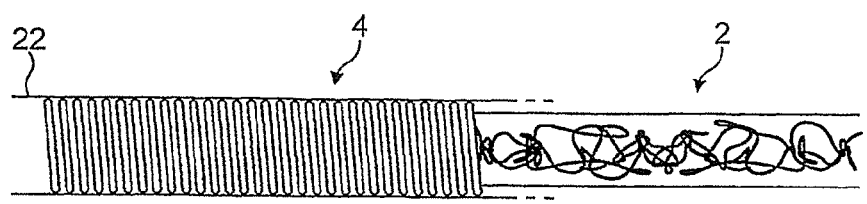
Figure 10:
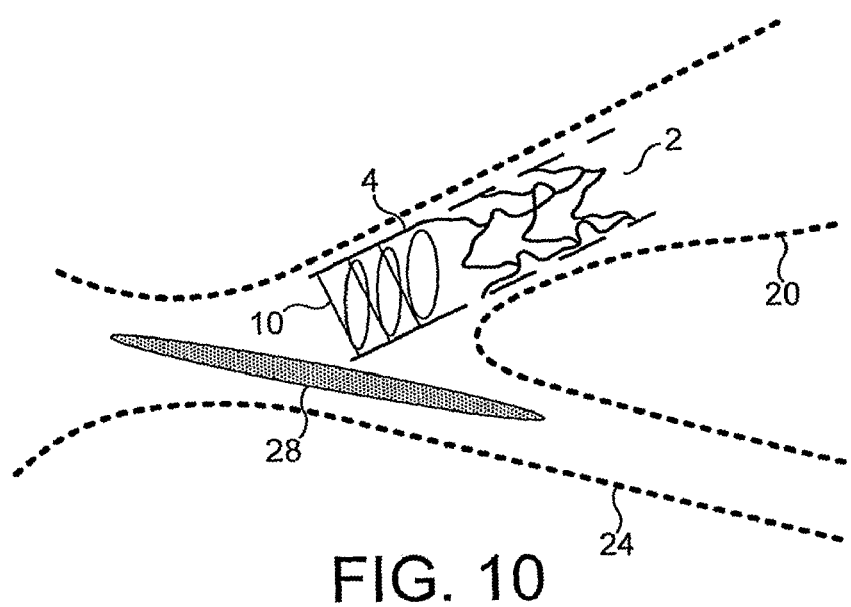
FIGS. 10 and 11 depict schematically an alternative procedure for stent placement.
Figure 11:
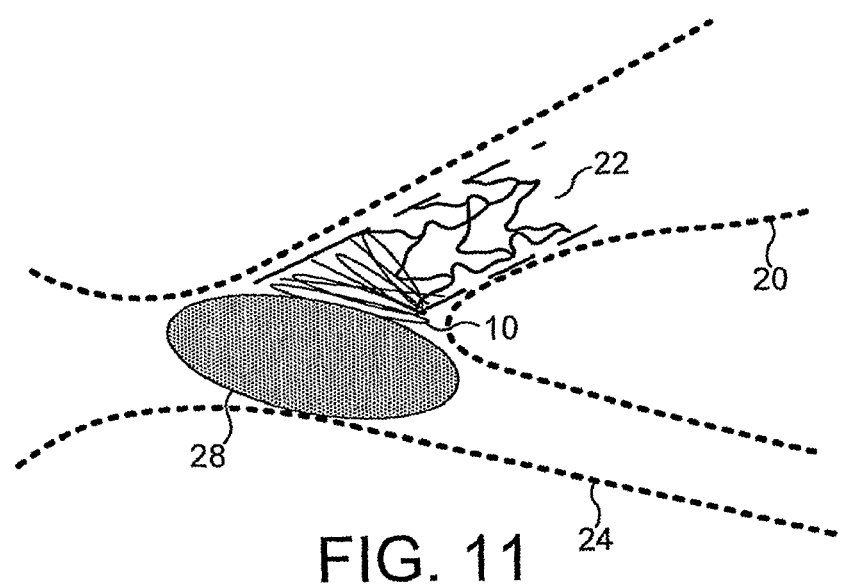

FIG. 9 depicts such a stent ready for placement including a spiral end portion 4 secured to a main portion 2 as described above, the spiral end portion 4 being constrained by a sheath 22 in a collapsed or unexpanded state. As will be described in more detail below, the stent can be placed by withdrawing the sheath with the stent in situ to allow the end portion to expand as far as possible given the constraint of being secured to the main portion, followed by expansion of the complete stent by balloon in a conventional manner.

The main portion 2 and end portion 4 described above may be manufactured in any suitable manner. The two portions may, for example, be manufactured from a single tubular member of appropriate material, for example stainless steel, cobalt chromium, Nitinol or Tantalum, or another suitable alloy by machining away a pattern such that the stent configuration remains, for example, by laser cutting.

Alternatively, the two portions may be manufactured separately and then secured to each other, for example, by welding. This allows greater flexibility in the choice of materials and manufacturing techniques. For example, as described above for the spiral embodiment of FIGS. 8 to 9, the main and end portions may be manufactured from different materials to allow different properties and manufacturing techniques. Application of this concept is, of course, not limited to this particular example. In the above example, the spiral end portion 4 is further manufactured in an expanded state and then collapsed and secured by a sheath and is made from a shape memory metal to allow subsequent expansion to the original configuration, while the main portion is manufactured as a conventional stent. The same technique may be applied to any of the other embodiments described above, manufacturing the end portion in an expanded state and then collapsing it and securing it using a sheath.

Further, it will be understood that the side branch stent may consist entirely of the end portion extending along all of its length without a separate main portion. This can result in an increased ease of manufacture. In yet a further alternative, the end portion and main portion may not be joined together but may be placed separately adjacent to each other in the side branch, that is, the repair in the side branch including a short stent consisting entirely of an end portion as described above and one or more separate main portion stents of conventional construction placed adjacent to each other.

Finally, the skilled person will be aware of any further, specific details of stent manufacture, examples of which can be found in US2004/0172126 (Hojeibane) and U.S. Pat. No. 6,673,107 (Brandt et al), both herewith incorporated by reference herein.

Figure 3:
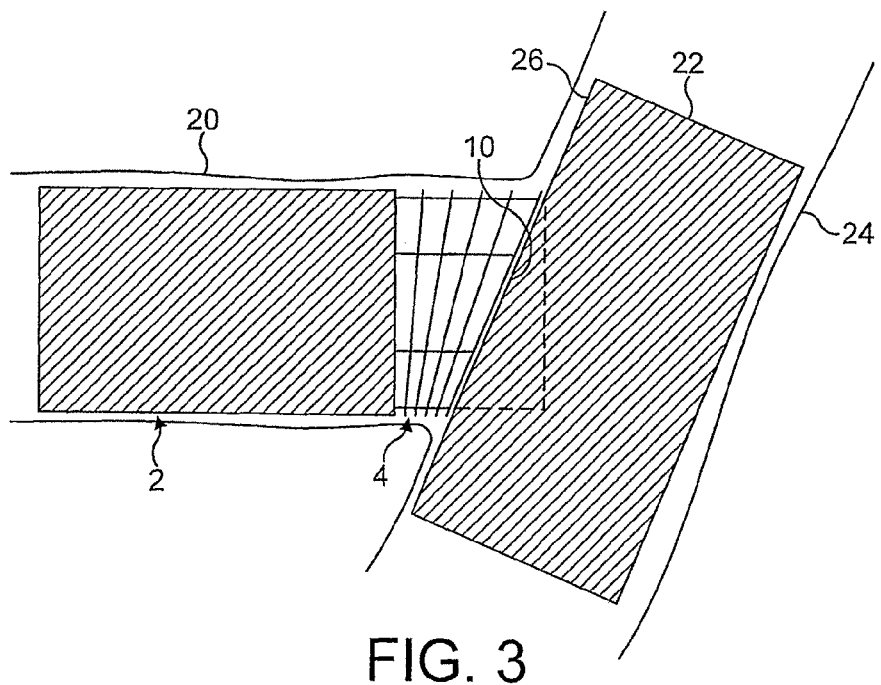
FIG. 3 illustrates the placement of the stent in a bifurcated vessel.

Turning now to the application of the stents described above, with reference to FIG. 3, a stent as described above is placed in a side branch of a bifurcated vessel which needs repair in a first step. The stent is placed such that all of the side branch and the ostium is fully supported by the stent as indicated by the dashed line in FIG. 3. In this sense, the placement is conventional using an angioplasty balloon catheter or, if applicable, the shape-memory of the stent by withdrawing a sheath and thereby heating it.

It will be understood that where the side branch stent includes an end and main portion of different material, for example, an end portion of shape memory material expandable by retraction of a sheath and a main portion expandable by balloon, the first step may include further sub-steps, for example a first sub-step of expanding the end portion by sheaf retraction and a second sub-step of expanding the main portion by balloon inflation. Similarly, where separate end portion and main portion stents are provided, the two stents may be expanded subsequently to each other using the respective appropriate method. It will, of course, be understood that in these cases expansion of the main portion or main portion stent (if separate stents are used) need not take place immediately after expansion of the end portion or end portion stent but can be carried out at any appropriate time in the procedure. Of course, it will be understood that more than one conventional main portion stent may be placed in sequence after the end portion stent if separate stent or stent segments are used.

In a second step, a conventional stent, for example, one adapted for side branchability via an appropriate side branch window (see for example Abizaid et al discussed above and herewith incorporated by reference herein), is placed in the main branch 24 across the ostium of the side branch 20 in a conventional manner by inflating an angioplasty balloon inside the stent 22, or allowing the stent to expand by virtue of its inherent elasticity or shape-memory, for example. As the stent 22 expands it will push against the free end 10 of the end portion 4, thereby deforming the end portion such that the free end 10 will abut the adjacent surface 26 of the stent 22. This avoids the stress applied to the vessel wall when a conventional stent is used in the side branch 20 and also the complication of using two stems in the main branch 24.

In a third step, the repair is completed by backing up the balloon used to inflate the stent 22 (or introducing a balloon 28 into the main branch if a self expanding stent 22 is used), navigating balloon 28 into the side branch and expanding the balloon to align the end portion 4 of the side branch stent with a corresponding window in the main branch stent 22.

The procedure may involve placing the side branch stent indicated above, wiring it to allow access to the side branch stent and ballooning from the main branch to the side branch subsequent to the deployment of the main branch stent to ensure good apposition of all stents to the vessel walls of the main and side branch.

Figure 8B:
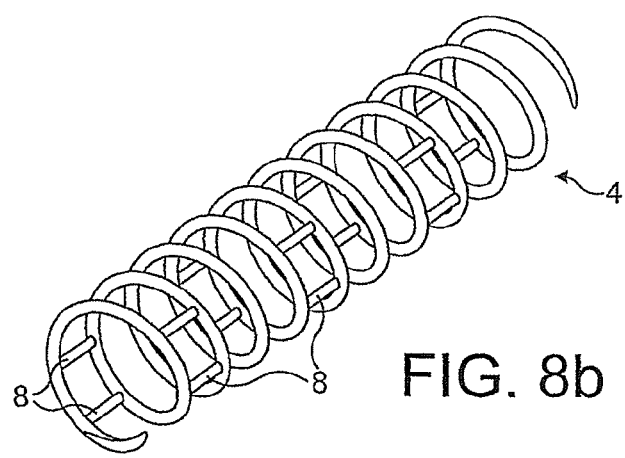

FIGS. 8 and 9 describe an alternative procedure in which the end portion 4 of the stent is shaped by an angioplasty balloon to conform to the ostium. Depending on the lesion, the repair may be limited in this way to the side branch, or an additional stent may then be introduced in the main branch, similar to the procedure described above.

It will be understood that the above description of specific embodiments of the invention is by way of example only and is not intended to limit the scope of the invention. Many modifications and alterations of the specific embodiments described above will be apparent to a person skilled in the art and are intended to be within the scope of the appended claims.

The invention claimed is:

1. A stent comprising:
an end portion which, in an expanded state, defines a vessel-supporting wall having a free end defining a circumference at the free end; wherein the end portion is configured to deform to longitudinally collapse the vessel-supporting wall at a first point on the circumference by a larger amount than at a second point, the end portion including an expandable ring secured by a collapsible web, wherein the ring is configured to expand due to collapsing of the web when the end portion is deformed by application of a force longitudinally collapsing the vessel-supporting wall at the first point by a larger amount than at the second point.

2. The stent as claimed in claim 1, wherein the free end defines a free end plane and wherein the end portion is deformable to dispose the end plane in a tilted relationship with respect to the vessel-supporting wall.

3. The stent as claimed in claim 2, wherein the free end is configured to be arranged to yield to an uneven pressure to result in the tilted relationship.

4. The stent as claimed in claim 2, wherein the free end is configured to yield in response to being pressed by a surface which is tilted with respect to the vessel-supporting wall to an attitude in which the end plane is generally aligned with the surface.

5. The stent as claimed in claim 2, wherein in response to the end plane being tilted, a projection of the free end on to a cross-section of the vessel-supporting wall substantially coincides with the cross section of the vessel-supporting wall.

6. The stent as claimed in claim 1, wherein the end portion defines a concertina-like arrangement.

7. The stent as claimed in claim 1, wherein the ring is configured to be folded up within the vessel-supporting wall.

8. The stent as claimed in claim 1, wherein the web is configured to fold onto itself when collapsing.

9. The stent as claimed in claim 8, wherein the web is configured to fold onto itself within the vessel-supporting wall.

10. The stent as claimed in claim 8, wherein the web is configured to fold onto itself to protrude from the vessel-supporting wall out of the end portion.

11. The stent as claimed in claim 1, wherein the end portion includes a plurality of expandable rings secured to each other by collapsible webs.

12. The stent as claimed in claim 1, further including a main portion configured to support a vessel, the end portion being secured to the main portion.

13. The stent as claimed in claim 12, wherein the main portion and the end portion are manufactured from a single tubular member by machining away material to define the main and end portions.

14. The stent as claimed in claim 12, wherein the main portion and the end portion are separately manufactured and joined.

15. The stent as claimed in claim 1, wherein the end portion is constrained by a sheath in its unexpanded state and is expandable by withdrawing the sheath.

16. The stent as claimed in claim 15, wherein the end portion comprises a shape memory alloy.

17. The stent as claimed in claim 1, wherein the collapsible web is jointed to enable folding of the web onto itself.

18. A method of utilizing a stent to repair bifurcated blood vessels, the method comprising the steps of:
providing a stent having an end portion which, in an expanded state, defines a vessel-supporting wall having a free end defining a circumference at the free end, the end portion including an expandable ring secured by a collapsible web;
longitudinally collapsing the vessel-supporting wall at a first point on the circumference by a larger amount than at a second point by deforming the end portion;
expanding the ring and collapsing the web upon deforming the end portion and collapsing the vessel-supporting wall, wherein the expansion of the ring is caused by the collapsing of the web.

19. The method of claim 18, wherein the free end defines a free end plane and wherein the end portion is deformed to dispose the end plane in a tilted relationship with the vessel-supporting wall.

20. The method of claim 19, wherein the free end yields to an uneven pressure to result in the tilted relationship.

* * * * *